United States Patent [19]

Zeikus

[11] Patent Number: 4,572,898
[45] Date of Patent: Feb. 25, 1986

[54] THERMOPHILE ISOLATE HAVING THERMOSTABLE HYDROLYTIC ACTIVITY

[75] Inventor: Joseph G. Zeikus, Madison, Wis.

[73] Assignee: Genentech, Inc., South San Francisco, Calif.

[21] Appl. No.: 449,716

[22] Filed: Dec. 14, 1982

[51] Int. Cl.$^4$ ............ C12N 9/24; C12N 1/20; C12R 1/145; C12P 7/06
[52] U.S. Cl. .................. 435/200; 435/168; 435/195; 435/201; 435/220; 435/139; 435/140; 435/161; 435/842; 435/253; 426/7
[58] Field of Search ................ 435/200, 842

[56] References Cited

U.S. PATENT DOCUMENTS

| | | | |
|---|---|---|---|
| 2,599,531 | 6/1952 | Smyth et al. | 435/200 |
| 3,058,890 | 10/1962 | Miura et al. | 435/200 |
| 4,200,694 | 4/1980 | Ishii et al. | 435/101 |
| 4,400,470 | 8/1983 | Zeikus et al. | 435/162 |

OTHER PUBLICATIONS

Enzyme Nomenclature, published 1979, pp. 236, 237, 286 and 287.
Lund; B. M. et al., "J. Gen. Microbiology", 104, 59, (1978).
MacMillan; J. D. et al., "Biochemistry", 3, 572, (1964).
J. Zeikus et al., "Arch. Microbiol.", 41–48, (1979).
J. Zeikus et al., "J. Bact.", 143, (1): 432–440, (1980).
J. Weigel et al., "Arch. Microbiol.", 128: 343–348, (1981).
J. Zeikus, "Ann. Rev. Microbiol.", 34: 423–464, (1980).
J. Zeikus, "Enzyme Microb. Technol.", 1: 243–251, (1979).

Primary Examiner—Lionel M. Shapiro

[57] ABSTRACT

This application represents an invention based upon the discovery of a novel thermophilic organism, its isolation from natural source and to the unique thermostable hydrolytic activity produced by this bacterium, this activity being useful for industrial purposes.

3 Claims, 8 Drawing Figures

THERMOPHILE ISOLATE HAVING THERMOSTABLE HYDROLYTIC ACTIVITY

FIELD OF THE INVENTION

The present invention is based upon the discovery of a new thermophile microorganism and its isolation from natural source. It is further directed to the unique thermostable hydrolytic activity produced by this bacterium and to the exploitation of this activity in industrial use.

BACKGROUND OF THE INVENTION

Recent history has witnessed an increase in research investigating the biology of thermophilic microorganisms. Their potential for use in process applications in biotechnology stems from their ability to grow at relatively high temperatures with attendant high metabolic rates, production of physically and chemically stable enzymes and elevated yields of associated end products (1). The emerging urgency to harness the power of these organisms in new industrial processes is a result of problems associated with noticeably diminishing resources of fossil fuels and food supplies and the proliferation of generated pollutants and wastes. Microbially based processes are thought to be an answer to these problems by efficient conversion of renewable wastes to useful chemicals and fuels. The reduction of pollutants generated from use of fossil fuels can be achieved by use instead of microbial energy.

Armed with such prospects, researchers have busied themselves with the study of thermophilic organisms (2 to 11) which, by deduction, would be expected to contribute stable, rapid and less expensive processes and would thus find useful applications in chemical feedstock and fuel production, bioconversion of wastes, enzyme technology and single cell protein production.

Specifically, attention has centered on bacterial species common to volcanic thermal spring ecosystems (12-17). Among those anaerobic species identified as active included *Thermobacteroides acetoethylicus, Thermoanaerobium brockii* and *Methanobacterium thermoautotrophicum*.

In addition, attention has focused on species of the genus *Clostridia* (C.), notably *C. thermocellum, C. thermohydrosulfuricum, C. thermosaccharolyticum,* and *C. thermoaceticum* and distinct microbial properties and characteristics for them have been detailed (18–23).

Again, focus has centered on microbes which may find use in the industrial production of methane, ethanol or acetic acid, as examples from the broad compass of potential utilities. It is recognized that hydrolytic activity is of general importance to the degradation of organic matter and as biochemical agents of plant spoilage or pathogenesis (24–27). It follows that enzymes displaying such activity may find useful applications in the food processing and agricultural industries.

The present invention is founded on the goal of identifying and isolating a microorganism whose characteristics and activities would match those useful for specific exploitation in industry.

The publications and other materials hereof used to illuminate the background of the invention and, in particular instances, to provide additional details concerning its practice are incorporated herein by reference, and for convenience, are numerically referenced parenthetically in the following text and respectively grouped in the appended bibliography.

SUMMARY OF THE INVENTION

As a primary aspect, the present invention is directed to a new thermophilic microorganism and to its isolation from natural source and its detailed morphological, cellular and metabolic characteristics, enabling the scientific conclusion that this new species is distinct from previously reported microorganism isolates.

In addition, the present invention is directed to the hydrolytic activity displayed by this new species and to the enzyme preparation per se produced by this species. Further, the present invention includes, as aspects, the use of the identified and isolated species as well as the enzyme preparation produced by this species in industrial applications, particularly in agricultural and food processing. In addition, the present invention focuses on the ability of this new species to convert thiosulfate to elemental sulfur, a utility finding application in pollution control measures.

The novel microorganism hereof is identified as *Clostridium thermosulfurogenes* sp. nov. (ther.mo.sul.fu.ro.-ge.nes. Gr. n. *thermos* heat; L.M. *Sulfur* sulfur; Gr. n. *gennaio* to produce: *thermosulfurogenes*, producing sulfur in heat. Further details are elaborated *infra*.

It will be understood that the present invention involves the various embodiments associated with the discovery of *Clostridium thermosulfurogenes* and its use in all respects and is not to be construed as limited to any specific aspect or embodiment except as defined by the lawful scope of the appended claims.

DESCRIPTION OF PREFERRED EMBODIMENTS

The novel *Clostridium thermosulfurogenes* hereof is characterized as follows: Cellular characteristics. Straight rods $0.5 \times >2$ $\mu$m. Gram negative. Logarithmic cells motile by peritrichous flagellation. Forms long filaments and deposits yellow elemental sulfur in the medium and cells when grown with thiosulfate. Swollen, white-refractile, spherical endospores formed. No outer wall membranous layer present in thin sections. Agar imbedded colonies are fluffy, 1–2 mm in diameter, and not pigmented. DNA base composition of 32.6 (0±0.04) mol percent G+C. Cytochromes and catalase negative.

Growth characteristics. Optimum temperature for growth is $\geq 60°$ C., maximum about 75° C., minimum about 35° C. pH range for growth: optimum 5.5–6.5, minimum >4.0 maximum <7.6. Obligate thermophile and anaerobe. Complete growth inhibition by either 100 $\mu$g/ml penicillin, streptomycin, cycloserine, tetracycline, chloramphenicol, 500 $\mu$g/ml sodium azide, 2 percent NaCl, or 0.2 at m $O_2$.

Metabolic characteristics. Chemoorganotroph. Utilizes a wide variety of carbohydrates as energy sources including pectin, O arabinose, cellobiose, xylose, galactose, glucose, mannose, maltose, starch, melibiose, sucrose, trehalose or esculin. No growth on $H_2/CO_2$, lactose, cellulose, tartrate, lactate, pyruvate, methanol or glycerol. Fermentation products of glucose are ethanol, $H_2$, $CO_2$, lactate and acetate. Methanol and isopropanol formed on pectin. Sulfate, sulfite and nitrite not reduced.

Habitat. Algal bacterial mat ecosystems associated with thermal, volcanic springs. Type strain 4B. This stain was isolated from Octopus Spring, Yellowstone National Park. U.S.A.

American Type Culture Collection

This organism has been deposited with the American Type Culture Collection, Rockville, Md. under No. 33743, deposited June 17, 1982, with restrictions relating to the filing of patent application.

The results presented herein demonstrate general hydrolytic activity, for example, pectinolytic, amylolytic and genatinolytic activities. Specifically, results presented herein demonstrate pectin methylesterase and polygalacturonate hydrolase activity in a thermophilic bacterium, a novel finding. Both enzyme activities were extremely stable and active at high temperature (i.e., $\geq 60°$ C.). It follows that this thermal stable pectinolytic activity should have utility in, for example, fruit juice clarification, food processing or agricultural food waste treatment.

Mesophilic Clostridium species vary in regard to the type of pectin depolymerizing enzymes produced. In this regard, $C.$ thermosulfurogenes utilizes the same enzymes as reported in $C.$ felsineum and $C.$ roeum (28); however, it does not form polygalacturonate lyase common to $C.$ multifermentans (29). The cellular distribution of pectinase activity in $C.$ thermosulfurogenes is similar to that of cellulase activity in $C.$ thermocellum (30). Notably, both of these thermophilic anaerobic species produce active, oxygen-insensitive extracellular depolymerases.

Two separate enzymes are suggested by the differences observed for temperature and activity profiles of pectin methylesterase and polygalacturonate hydrolase. Nonetheless, both activities were expressed during growth on polygalacturonate although pectin methylesterase is of no catalytic use on this substrate. Also, both activities were recovered in one 320,000 MW peak from gel filtration on Sephadex G200.

DETAILED DESCRIPTION

Chemicals. All chemicals used were reagent grade and were obtained from either Mallinckrodt (Paris, KY, U.S.A.) or Sigma (St. Louis, MO, U.S.A.). Pectin was obtained from Sunkist Growers (Corona, CA, U.S.A.). Agar, tryptone and yeast extract were obtained from Difco (Detroit, MI, U.S.A.). All gases were obtained from Matheson (Joliet, IL, U.S.A.) and were purified free of oxygen by passage over heated (370° C.) copper filings.

Inocula and bacterial strains. Two thermophilic strains were enriched from a 60° C. site in the Octopus Spring algal bacterial mat in Yellowstone National Park, WY, U.S.A., employing anaerobic procedures described previously (1,16). Both isolates had identical properties. Data presented are for one, type strain 4B.

Culture techniques and media. Anaerobic procedures used for cell cultivation and media preparation were described previously (16,31). The low phosphate buffered basal medium (LPBB medium) (described in (1)) was used with a $N_2/CO_2$ (95/5) gas phase. When needed, carbohydrates (0.5 percent), tryptone (1 percent) or yeast extract (0.3 percent) were autoclaved separately and added by syringe to the final concentrations indicated by syringe. Medium (described in (30)) was used to examine cellulose fermentation, and Medium 77 (32) was used to test sulfate reduction but glucose was substituted for lactate. Routine cell maintenance and experimental analysis was performed in anaerobic culture tubes (23 ml volume, 18×142 mm) obtained from Bellco Glass Co., (Vineland, NJ, U.S.A.) that contained 10 ml of medium, and which were sealed with black rubber bungs. Prior to inoculation culture medium was reduced by the addition of sodium sulfide (0.05 percent final concentration). Test medium for quantification of thiosulfate reduction contained LPBB medium with 0.3 percent yeast extract; 0.05 percent $FeSO_4$, 0.02 percent sodium thioglycolate, and 0.02 percent ascorbic acid, but no sodium sulfide was added. Cultures were routinely incubated without shaking at 60° C. unless indicated in the text. For isolation of colonies in anaerobic roll tubes LPBB medium was supplemented with 0.5 percent glucose, 0.1 percent yeast extract and 2.0 percent purified agar. Large quantities of cells were grown at pH 7.0 with mixing in a MicroFerm Fermentor (New Brunswick) that contained 12 L of LPBB medium, 0.5 percent glucose and 0.1 percent yeast extract.

Cellular characterization. A Carl Zeiss photomicroscope was used for phase contrast and bright field observations including determination of cell size. Agar coated glass slides were utilized to obtain long filaments in focus for photo-microscopy.

The methods used for preparing cells for thin sectioning and electron microscopic examination are known per se (33). Cells were prefixed for 2 min in 0.1 percent osmium tetroxide, washed in acetate veronal buffer, suspended in agar, and then fixed overnight in 1 percent osmium tetroxide. All preparations were examined with a Siemens 101 electron microscope.

DNA was isolated and purified from lysozyme treated cells by known methods (34). DNA base compositions were calculated (according to (35)) in 0.015 M NaCl and 0.0015 M trisodium citrate as determined in a Gilford Model 250 spectrophotometer equipped with a Model 2527 thermoprogrammer. *Escherichia coli* DNA VIII lot No. 57C-6830 from Sigma Chemical Co., (St. Louis, MO, U.S.A.) served as standard. DNA reported represents the mean of 4 separate determinations. The percent G+C of *E. coli* standard was 53.9 ($\pm 1.0$ percent).

Cytochromes were identified in air versus dithionite reduced difference spectra of cell extracts analyzed with a Beckman model 25 scanning spectrophotometer. Cell extracts were prepared by sonicating a suspension of 1 g wet weight cells in 5 ml 50 mM potassium phosphate buffer and retaining the supernatant after centrifugation at 10,000 G for 15 min in a Sorvall centrifuge. Protein was determined in extracts (36).

Growth and metabolic characterization. Growth was determined by measuring the increase in turbidity at 660 nm. Optical density was quantified directly by insertion of the anaerobic culture tubes into a Spectronic 20 spectrophotometer (Bausch and Lomb, Inc.).

Fermentation metabolites were measured directly in liquid or gas samples removed from the culture tubes by syringe. Alcohols and acids were measured by the gas chromatography-flame ionization detection procedures (described in (1)). All gases were quantified by the gas chromatography-thermal conductivity detection methods (37). Lactate was measured spectrophotometrically by the D- or L-lactate dehydrogenase assay (38). Glucose consumption was determined by reducing sugar analysis with dinitrophenyl salicylic acid (39).

Protein was determined by the Biuret method modified for sulfur containing solutions (40). This method uses a control for non-protein dependent color formation by destruction of the color complex via addition of potassium cyanide. Thiosulfate, sulfite, and sulfide were determined in cell free culture fluids (41). Sulfur was determined in culture fluid by extraction with carbon disulfide and spectrophotometric analysis (42).

Isolation and Cultivation

The organism was selectively enriched from the Octopus Spring algal bacterial mat by serial dilution of the source inoculum in LPBB medium that contained 1.0 percent tryptone; 0.3 percent yeast extract and 0.5 percent pectin. The last positive tube (i.e., $10^{-3}$ dilution) that displayed growth and gas production was repeatedly transferred on LPBB medium containing 0.1 percent yeast extract and pectin. The organism was isolated by serial dilution in agar roll tubes with LPBB, 0.1 percent yeast extract and 0.5 percent glucose medium followed by transfer of single colonies to homologous liquid medium.

Single colonies were light yellow, 0.5–1.5 mm in diameter and exhibited a fluffy, brush-like appearance. The organism formed large colonies on agar plates incubated in an anaerobic chamber. Stock cultures maintained viability when held at room temperature or at 4° C. for two weeks. Permanent stocks were kept for more than 6 months by freezing anaerobic cell suspensions in 20 percent glycerol at −80° C.

Cellular Properties

Figure 1:
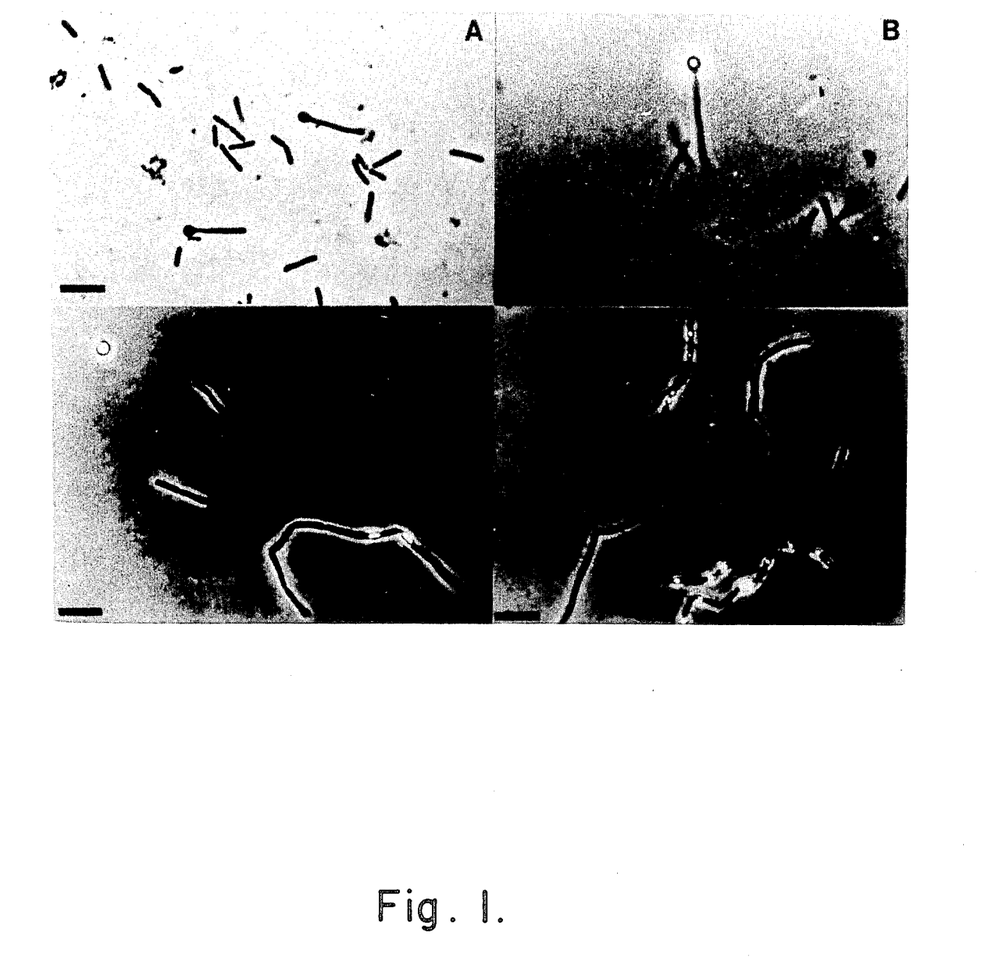
FIG. 1 represents phase contrast photomicrographs of $C.$ thermosulfurogenes. A. and B. Sporulating cells grown in LPBB, 0.2 percent xylose and 1.0 percent MOPS buffer medium C. D. Sulfur depositing cultures grown on LBPP, 0.5 percent glucose, 0.1 percent yeast extract and 20 mM $Na_2S_2O_3$. Note that phase bright sulfur accumulates in the medium on or within cells. Bar represents $\mu$m.

The morphological features of *C. thermosulfurogenes* varied considerably with the age of cultures and the specific growth medium used (see FIG. 1). Exponential phase cells grown on glucose LPBB-yeast extract medium were actively motile by peritrichous flagellation, phase dark, and stained gram negative. Stationary phase cells were more phase light in appearance and contained dark granules. Cells existed as rods that varied considerably in length depending on the medium (i.e., as single short rods of 2 $\mu$m to filamentous chains greater than 20 $\mu$m). Sporulation was never observed in glucose media but was detected in late stationary phase cultures grown with xylose or pectin as the energy source. Sporulation was especially favored in LBPP medium that contained 0.1 percent yeast extract, 0.2 percent xylose and 1.0 percent MOPS Buffer. Sporulating cells were on the average larger than vegetative cells and formed swollen, terminal, spherical spores (FIG. 1B). Only a few sporulating cells became distinctly phase bright and white in old cultures and free spores were rare.

Most notably, the addition of sodium thiosulfate at 20 mM resulted in very turbid cultures (i.e., O.D. 660>2.0) that contained a white-yellow precipitate at the end of growth. Microscopic analysis of these cultures revealed the presence of yellow elemental sulfur granules in both the medium and on or within cells (C, D).

Figure 2:
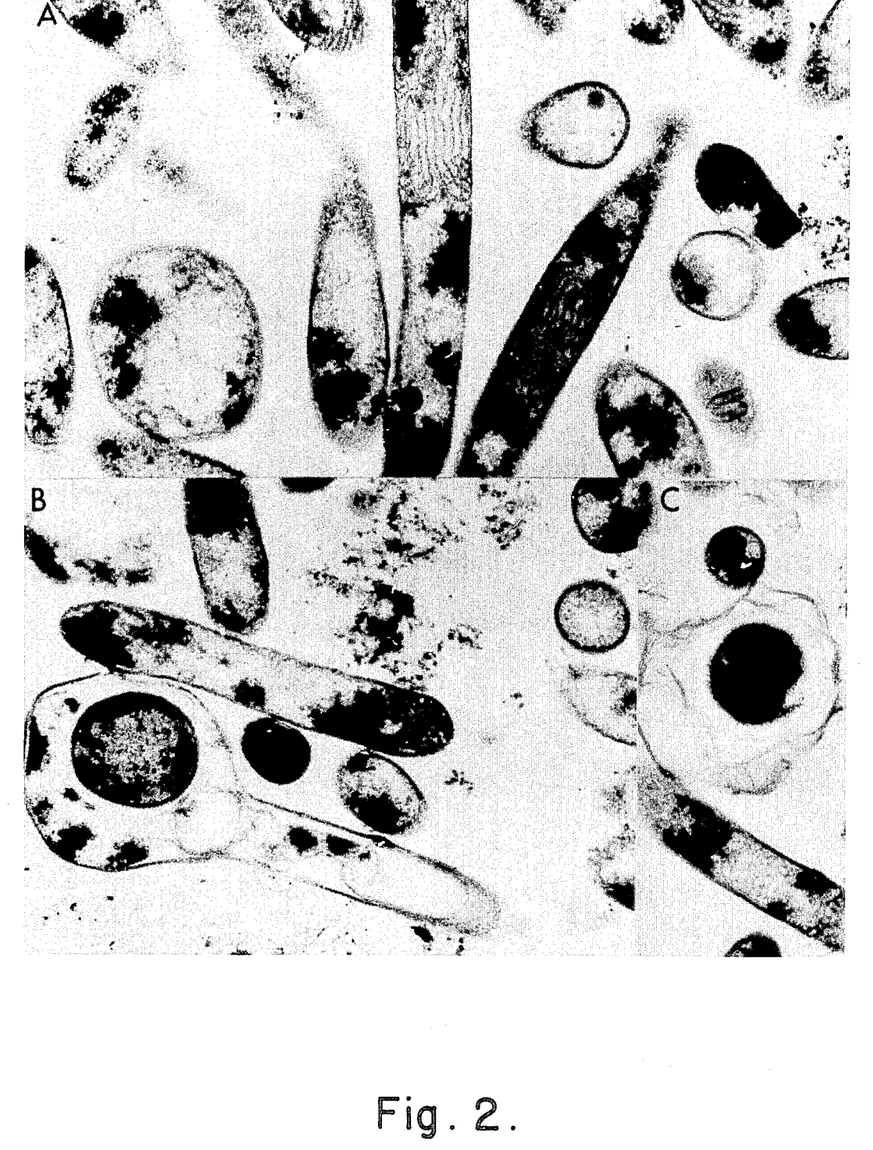
FIG. 2 are electron micrographs of thin sections of $C.$ thermosulfurogenes grown on LPBB, 0.3 percent xylose, 0.2 percent yeast extract medium. A. Grazing cells illustrating internal membranes. B. Sporulating cultures showing a swollen sporangium (S) and vegetative cell (V). Arrows point to double tract appearing wall layers. C. Free spore illustrating electron transparent spore cortex and external coat layers. Bar represents $\mu$m.

Electron microscope analysis of *C. thermosulfurogenes* in thin section revealed some architectural features that were not typical of other Clostridia (FIG. 2). Notably, internal membranes were very numerous and often appeared vesicular. The cell wall was thin and poorly discernible but displayed a double layered wall common to most Clostridia. Unlike many other gram negative staining bacteria no outer wall membrane layer was present. Large, electron dense cytoplasmic granules were common in cells. All spores were spherical and swollen but most appeared abortive because of the absence of an electron transparent spore cortex.

DNA isolated from *C. thermosulfurogenes* had a base composition of 32.6±.04 mol percent guanosine plus cytosine. Difference spectra of crude cell extracts did not display absorbance bands corresponding to cytochromes. Cells lacked catalase. Cell proliferation was not detectable in the presence of: either 100 $\mu$g/ml culture cycloserine, penicillin, streptomycin, tetracycline or chloramphenicol; 500 μg/ml sodium azide; 2 percent sodium chloride; and 21 percent $O_2$ in the culture headspace.

Growth and Metabolic Properties

Figure 3:
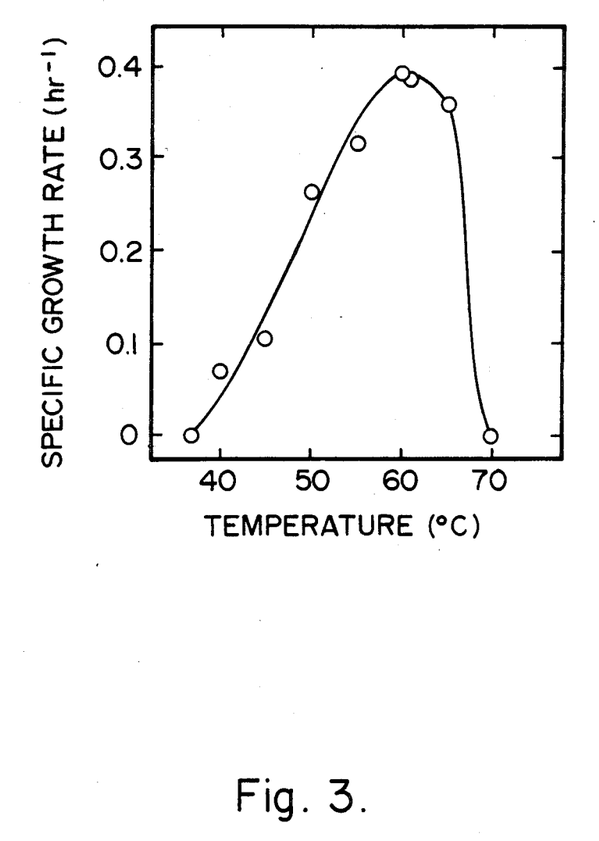
FIG. 3 shows the relationship between temperature and growth rate of $C.$ thermosulfurogenes. Experiments were performed in anaerobic culture tubes that contained 10 ml of LPBB medium with 0.5 percent glucose and 0.3 percent yeast extract.
Figure 4:
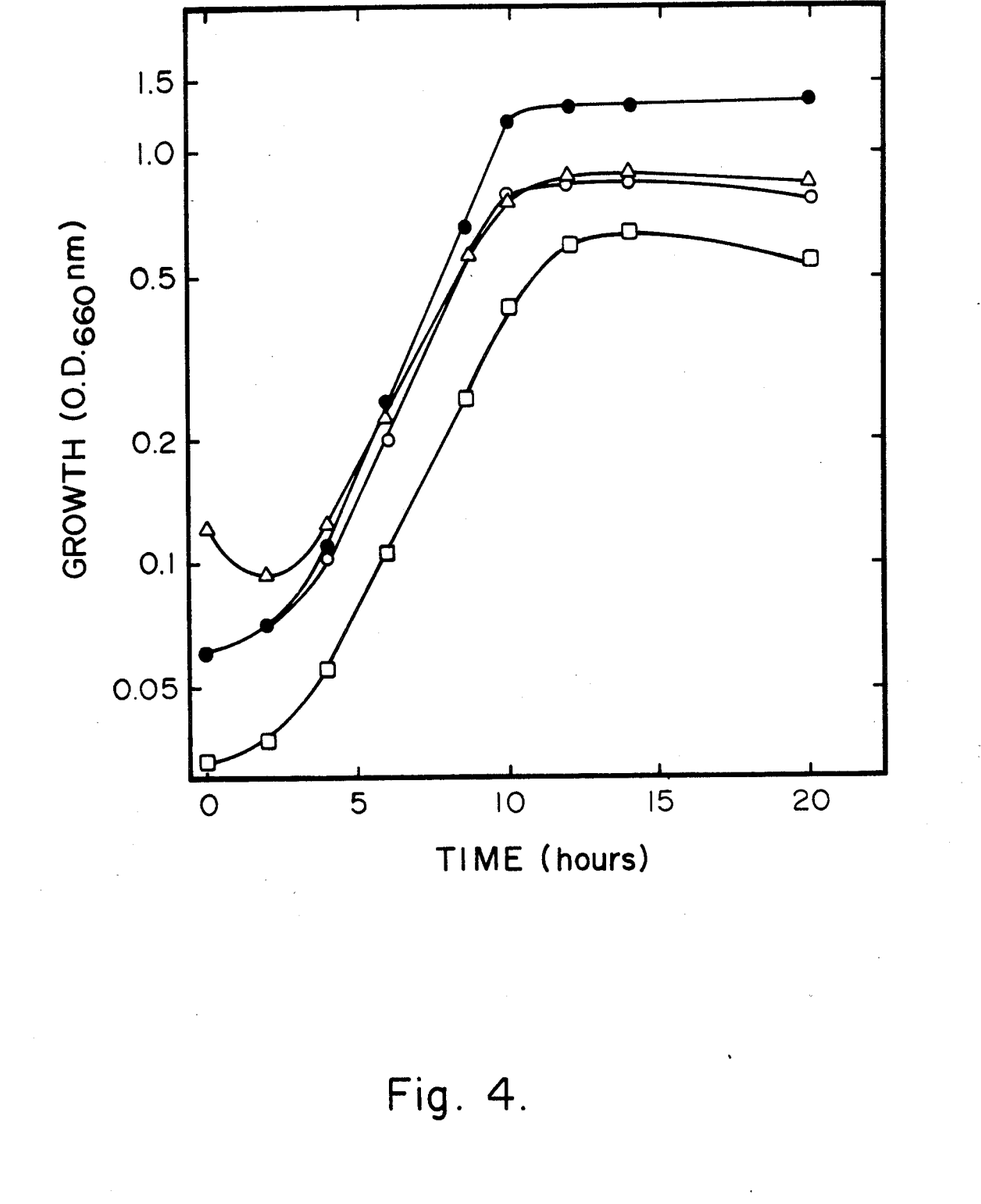
FIG. 4 demonstrates the relationship between nutrient source and growth of $C.$ thermosulfurogenes. Symbols indicate the following growth media: ●—●, LPBB, 0.5 percent glucose 0.3 percent yeast extract and 1.0 percent tryptone; 0—0, LPBB, 0.5 percent glucose and 0.3 percent yeast extract; $\Delta$—$\Delta$, LPBB, 0.5 percent pectin and 0.3 percent yeast extract; and, □—□, LPBB and 0.5 percent glucose. Experiments were performed in anaerobic culture tubes that contained 10 ml media and 1 ml of medium growth on LPBB medium with 0.5 percent glucose and 0.1 percent yeast extract.

The dependence of growth rate on temperature is shown in FIG. 3. The optimum temperature for growth of C. thermosulfurogenes was near 60° C., the maximum was below 75° C. and the minimum above 35° C. The growth rate and yield (i.e., optical density) of C. thermosulfurogenes varied with the nutrient sources applied (see FIG. 4). The growth rate and yield was lowest on mineral medium with ammonium as nitrogen source and highest in complex medium with tryptone and yeast extract. The organism was repeatedly transferred (20 times) on glucose and mineral medium. In complex medium the cell doubling time on polymeric pectin (2.1 h) was only slightly higher than that on glucose (1.9 h). The optimum pH for growth on glucose was 5.5–6.5; and, growth was not observed below 4.0 or above 7.6.

C. thermosulfurogenes fermented a wide variety of energy sources including: L-arabinose, cellobiose, galactose, glucose, inositol, mannitol, maltose, melibiose, rhamnose, sucrose, trehalose, D-xylose, starch, pectin, polygalacturonic acid, amygolain, esculin, and salicin. Cellulose, mannose, arabinogalactan, galacturonate, citrate, pyruvate, lactate, tartrate, lactose, melezitose, raffinose, D-ribose, sorbitol, methanol, glycerol were not fermented. The organism liquified gelatin but neither produced indol, acetylmethylcarbinol or hydrogen sulfide nor reduced sulfate or nitrate. The organism actively hydrolyzed pectin, starch and gelatin during growth.

The main products of carbohydrate fermentation by C. thermosulfurogenes were $H_2/CO_2$, ethanol, acetate and lactate (see Table 1). Notably, on pectin as energy source, both methanol and isopropanol were formed. Considerably more ethanol and lactate were produced on glucose than on polygalacturonate, which is a more oxidized substrate. The fermentation balance calculated on glucose was 242 glucose→231 $H_2$ + 207 ethanol + 152 acetate + 113 lactate + 317 $CO_2$. This accounted for a carbon recovery of 95 percent and oxidation reduction index of 0.98.

Figure 5:
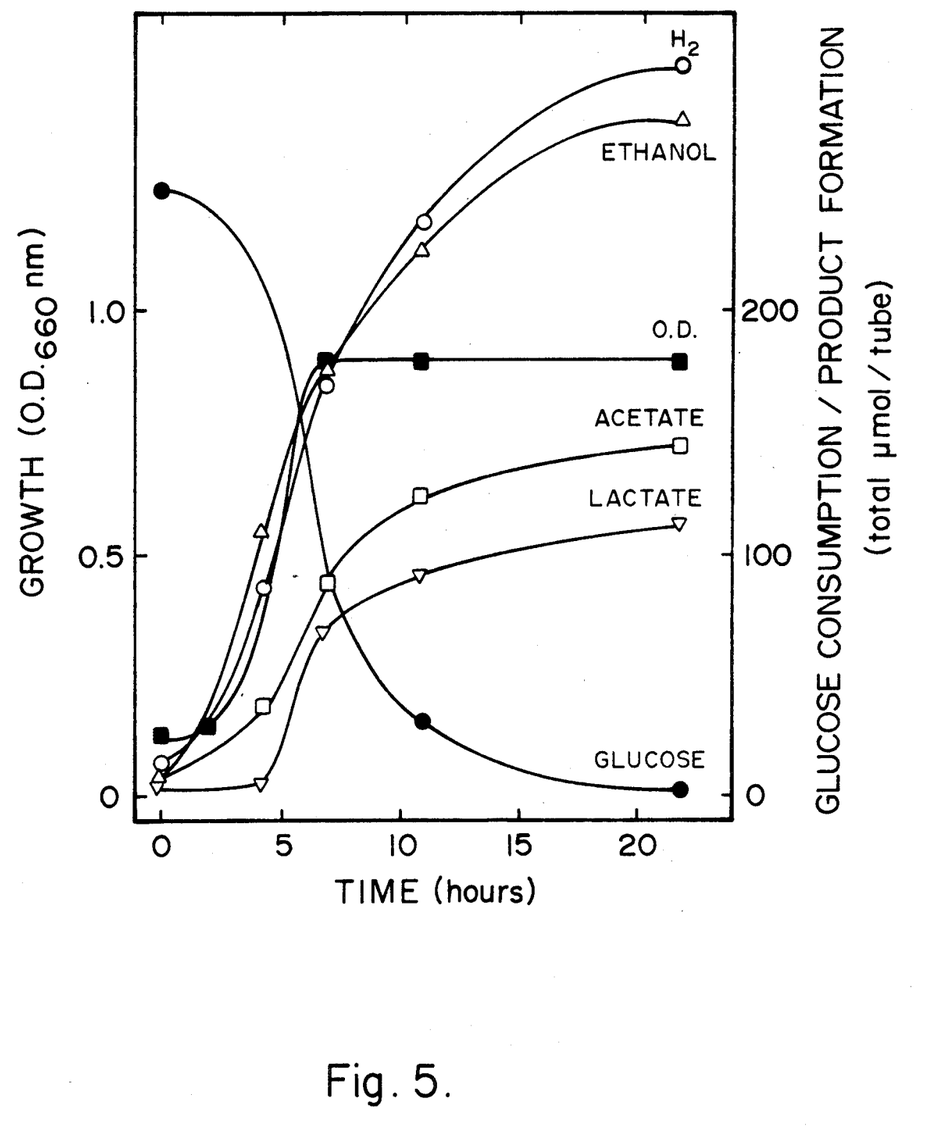
FIG. 5 is a glucose fermentation time course of $C.$ thermosulfurogenes. Experiments were performed in anaerobic culture tubes that contained LPBB medium with 0.3 percent yeast extract and 0.5 percent glucose.

The dependence of fermentation product formation on growth is shown in FIG. 5. All end products increased in response to growth and glucose consumption. However, both glucose consumption and end product formation continued after growth ceased. Growth appeared uncoupled by the high proton concentration (i.e., pH<4.5) in the medium. Growth on glucose at pH 7.0 was not inhibited by normal end product concentrations of ethanol, acetate, lactate or by 3 atmospheres of $H_2/CO_2$.

Table 2 demonstrates the type of thiosulfate transformation exhibited by C. thermosulfurogenes. In the absence of thiosulfate, growth occurred without formation of inorganic sulfur metabolites; however, growth was not as good as in the medium with cysteine or sodium sulfide as reducing agent. Notably, the addition of increasing amounts of thiosulfate increased the culture turbidity but not the total cel protein formed. Thiosulfate was converted to elemental sulfur but neither sulfite nor sulfide was produced. The addition of sulfite inhibited growth but it was not converted to elemental sulfur.

TABLE 1

Relationship between energy source and fermentation products formed by C. thermosulfurogenes[a]

| Substrate | Hydrogen | Methanol | Ethanol | Acetate | Lactate | Isopropanol | $CO_2$ |
|---|---|---|---|---|---|---|---|
| | | | End Products (total umol/tube) | | | | |
| Glucose | 231 | — | 207 | 152 | 113 | — | 317 |
| Pectin | 316 | 113 | 22 | 190 | 28 | 12 | 212 |
| Polygalacturonate | 239 | — | 37 | 265 | 23 | — | 195 |
| Xylose | 173 | — | 220 | 175 | 19 | — | N.D. |
| Arabinose | 168 | — | 222 | 194 | 113 | — | N.D. |

[a]All experiments were performed in anaerobic culture tubes that contained 10 ml of LPBB medium, 0.3 percent yeast extract and 0.5 percent carbohydrate. Products were analyzed after 24 h incubation at 60° C.

TABLE 2

Inorganic Sulfur Transformations of C. thermosulfurogenes[a]

| Medium Additions (mM) | Turbidity (O.D. 660 nm) | Growth Protein (mg/ml) | Sulfur Metabolites | | | |
|---|---|---|---|---|---|---|
| | | | $S_2O_3^{-2}$ | $SO_3^{-2}$ | $S°$ | $S^{-2}$ |
| None | 0.54 | 0.17 | N.D. | 0.03 | 0.01 | 0.011 |
| $Na_2S_2O_3$ | 0.96 | 0.17 | 7.9 | 0.28 | 3.15 | 0.19 |
| 12.5 | 1.2 | 0.17 | 11.3 | 0.42 | 11.85 | 0.013 |
| 25 | 0.14 | 0.08 | N.D. | 18.7 | 0.1 | 0.022 |
| 25 (Control) | | | | | | |
| $Na_2SO_3$ | 0.36 | 0.08 | N.D. | 18.7 | 0.1 | 0.022 |
| 20 | | | | | | |

[a]All experiments were performed in anaerobic culture tubes that contained 10 ml of LPBB medium, 0.1 percent yeast extract and 0.5 percent glucose; but with a Fe-$SO_4$/thiosulfate/ascorbate reducing agent in lieu of $Na_2S$. Products were analyzed after 24 h incubation at 60° C. Controls were inoculated but treated the same way as other tubes. N.D. means not determined.

The discovery of C. thermosulfurogenes extends both the diversity of known anaerobic thermophiles and the described microbial sulfur transformation reactions. The transformation of inorganic sulfur compounds into elemental sulfur is performed by a limited number of microbial groups. The deposition of elemental sulfur within cells or culture media appears limited to anaerobic phototrophic bacteria (43) and aerobic Thiobacillus species, (44). However, these kinds of bacteria utilize reduced sulfur compounds as electron donors. C. thermosulfurogenes is the first fermentative chemoorganotrophic bacterium reported to form sulfur from thiosulfate. This transformation is especially novel because no sulfide or sulfite was detected during the conversion of thiosulfate to sulfur.

The presence of C. thermosulfurogenes appears of importance to the algalbacterial mat ecosystem. The chemical composition of the major particulate fraction of primary production in this 55°–65° C. ecosystem (i.e., microbial cell wall layers) is not cellulose but, rather, carbohydrate and peptideglycan polymers. Although other fermentative anaerobes such as C. thermohydrosul-

*furicum, T. acetoethylicus, T. brockii* and *M. thermoautotrophicum* have been isolated from this environment, none of these strains can degrade pectin. Thus, pectin decomposition is of importance to prevent organic matter accumulation in this ecosystem where primary production and organic mineralization appear well-coupled (17). *C. thermosulfurogenes* appeared as the prevalent pectinolytic anaerobe and was present at $\geq 10^3$ cells/ml algal mat. However, this species is present in much lower numbers than total anaerobes (i.e., $\geq 10^8$ cells/ml algal mat, (16).

*C. thermosulfurogenes* was clearly distinguishable from the other described thermophilic saccharolytic *clostridium* species examined by electron microscopy. It contained a double-layered wall architecture but did not possess an outer wall membrane layer common to gram-negative staining anaerobes, e.g., *Bacteroides* or *Desulfovibrio*. Since it produced ethanol as the major soluble reduced end product of growth, and not butyrate or acetate, it is not similar to *C. thermosaccharolyticum* or *C. thermoaceticum*. The lack of cellulose fermentation, motility, and spherical spore formation distinguishes it from *C. thermocellum*. It bears closest resemblance to *C. thermohydrosulfuricum* in substrate utilization range and fermentation end products, but it forms elemental sulfur from thiosulfate rather than $H_2S$. Other significant differences between the Octopus Spring strains of *C. thermosulfurogenes* and *C. thermohydrosulfuricum* include: lack of growth inhibition by hydrogen, morphological features of sporogenesis, and the ability to liquify gelatin and to ferment pectin. The ability of *C. thermosulfurogenes* to form methanol as a major fermentation product of pectin is a consequence of pectin methylesterase activity and the absence of methanol consumption by described pectinolytic bacteria.

Activity Determination

Pectinase activities were analyzed utilizing either: cells in culture fluid directly; cells resuspended in buffer after centrifugation of cultures at 12,000Xg for 10 min; the decanted supernatant after centrifugation of cultures; crude extracts prepared by passage of cell-buffer suspensions through a French pressure cell at 48,800 KM/m² followed by centrifugation at 15,000 xg for 10 min; or membrane-buffer suspensions obtained after ultracentrifugation of crude extract at 120,00 xg for 2 hr. Unless indicated pectin enzymes were assayed at 60° C. in the presence of air. Pectin methylesterase was analyzed either by measuring the release of methanol or measuring pH change caused by the formation of free carboxylic groups (45). Polygalacturonate hydrolase was measured by detection of reducing sugars formed in 50 mM potassium acetate buffer (pH 5.0) containing 1 mM NaHSO₃ (46). Polygalacturonate lyase was measured spectrophotometrically at 235 nm by the method of Kurowski and Dunleavy (47). One unit of pectinase activity represents one umol of methanol or reducing sugar formed per minute. The protein content of cell extract (determined by (48)).

*C. thermosulfurogenes* produced both pectin methylesterase and polygalacturonate hydrolase during growth on pectin; but polygalacturonate lyase activity was not detected in controls (Table 3). The pectinolytic enzymes were present extracellularly in the culture fluid and within the cells. Notably, polygalacturonate hydrolase activity was higher in stationary versus log phase cultures; whereas, the converse was true for pectin methylesterase. Also, the ration of extracellular to cell bound activity was greater for pectate hydrolase than methylesterase. Neither activity was significantly present in the membrane fraction obtained from cell extracts. In similar experiments to those present in Table 3 O pectinase activities were not detected when cells were grown on glucose but both activities were present when cells were grown on polygalacturonate.

Figure 6:
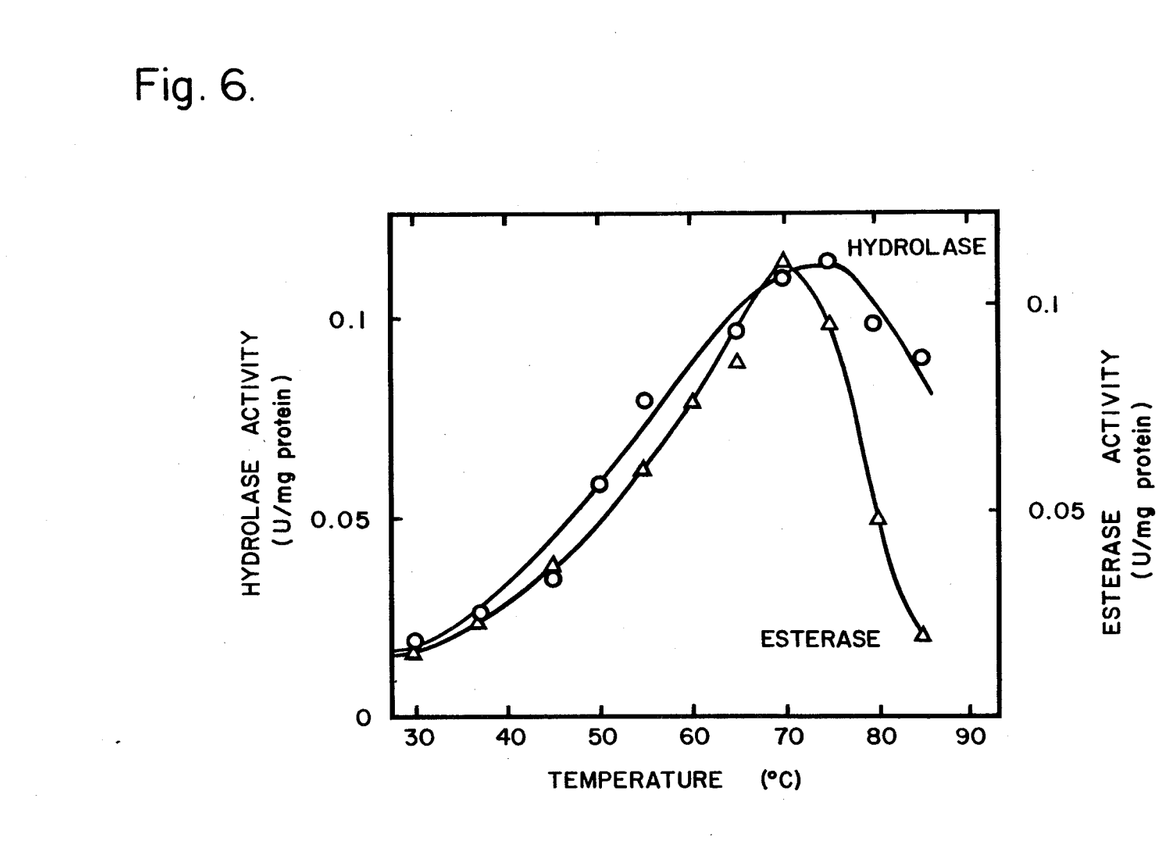
FIG. 6 shows dependence of pectinolytic enzyme activity of $C.$ thermosulfurogenes on temperature. Polygalacturonate hydrolase was assayed at pH 5.5 in 50 mM potassium acetate buffer and pectin methylesterase at pH 7.0 in 50 mM potassium phosphate buffer. Assays (total volume ml) used 200 $\mu$l cell extract (2.7 mg protein/ml).
Figure 7:
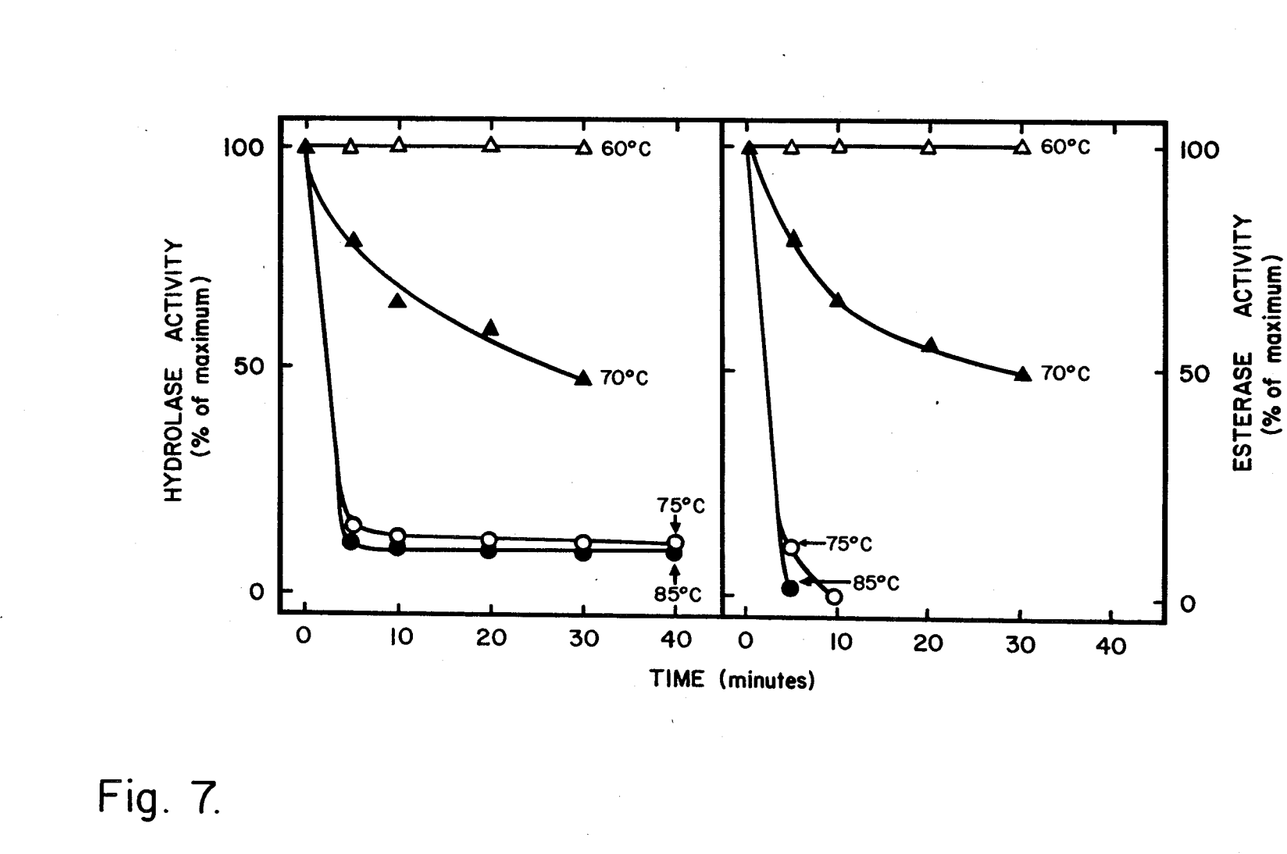
FIG. 7 depicts thermal stability of pectinolytic enzymes of $C.$ thermosulfurogenes. Cell extracts (1.7 mg protein/ml) was incubated at respective temperatures. Samples (200 $\mu$l) were withdrawn with time and assayed as described. Maximum activity was U/mg for polygalacturonate hydrolase at pH 5.5 and 60° C., and U/mg for pectin methylesterase at pH 7.0 and 60° C.

The relationships between temperature and pectinolytic activity of *C. thermosulfurogenes* cell extracts is shown in FIGS. 6 and 7. The optimum temperature for polygalacturonate hydrolase activity was 75° C., whereas pectin methylesterase activity was maximal at 70° C. Both enzyme activities were completely stable to heating at 60° C. for 30 min., lost 50 percent of activity at 70° C. and were effectively destroyed at $\leq 75°$ C.

Figure 8:
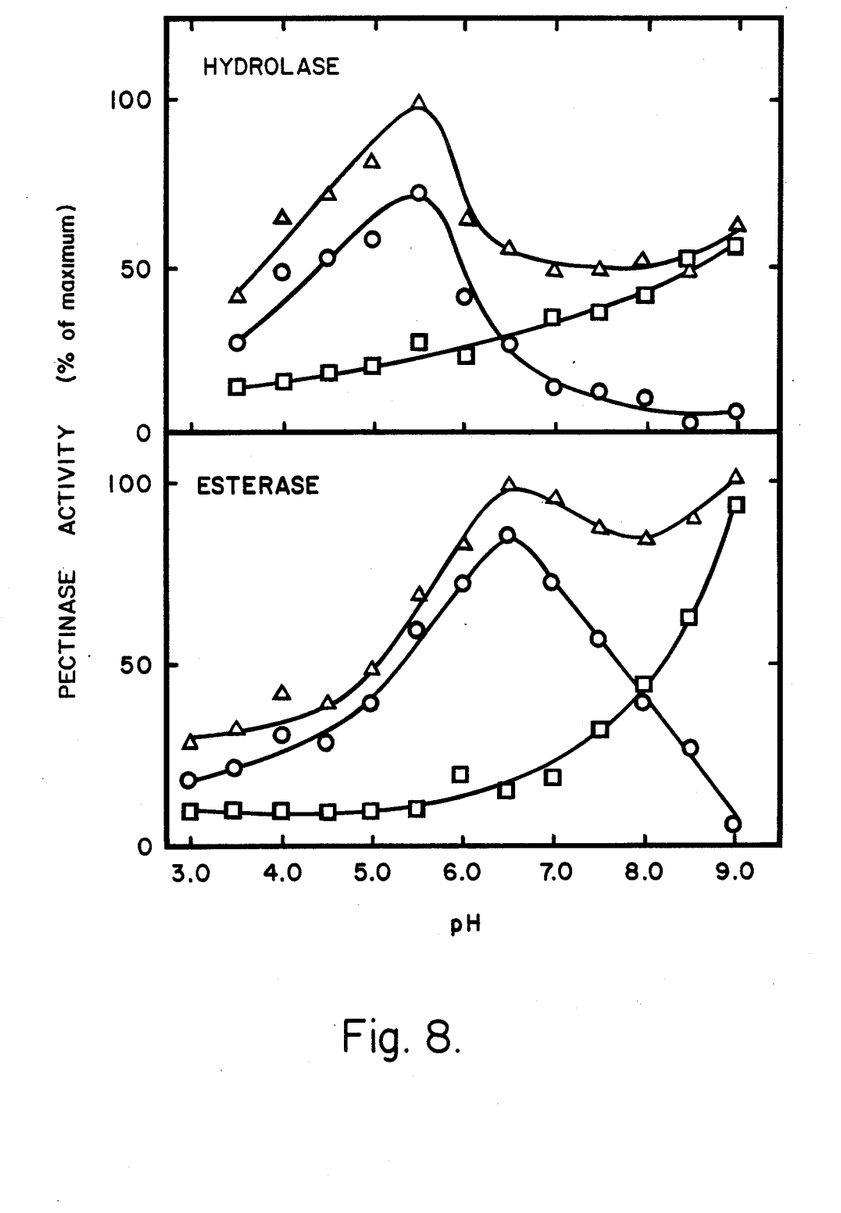
FIG. 8 depicts dependence of pectinolytic enzyme activity of $C.$ thermosulfurogenes on pH. Each activity was measured at 60° C. in a combined buffer solution that contained 50 mM each of potassium acetate, potassium phosphate, and trihydroxymethylaminomethane. Assays (total column ml) used 200 $\mu$l cell extract (3.24 mg protein/ml). Maximum activity was 0.29 U/ml for polygalacturonate hydrolase, and 0.21 U/ml for pectin methylesterase. Symbols: (□—□), control with boiled cell extracts; ($\Delta$—$\Delta$), cell extracts; (O—O ), cell extract minus control.

FIG. 8 illustrates the different pH optimum displayed by pectin methylesterase and polygalacturonate hydrolase activity of cell extracts. Notably, at alkaline pH values and 60° C. assay temperature employed, considerable non-enzymatic degradation of pectin occurred (i.e., as shown in the controls with boiled extracts). The pH optima for polygalacturonate hydrolase and pectin methylesterase were 5.5 and 6.5 as calculated by subtracting the control value from that of the experimental.

TABLE 3

Distribution of Pectinolytic Enzymes in *Clostridium thermosulfurogenes*[a]

| Assay | Culture | Location of Enzyme Activity (U/ml at 60° C.) Culture Supernate | Cell Suspension |
|---|---|---|---|
| I. Pectin Methylesterase | | | |
| Log phase | 0.38 | 0.22 | 0.17 |
| Stationary phase | 0.11 | 0.04 | 0.04 |
| II. Polygalacturonate Hydrolase | | | |
| Log Phase | 0.10 | 0.08 | 0.03 |
| Stationary phase | 0.15 | 0.13 | 0.04 |

[a]Conditions: cultures were grown at 60° C. in serum bottles that contained 50 ml of LPBB medium with 0.1 percent yeast extract and 0.5 percent pectin. Samples of Log phase cultures (O.D.$_{660}$nm = 0.55) were obtained at 7 h incubation; whereas, stationary phase cultures were taken at 20 h.

In other experiments with culture filtrates the same pH and temperature optima were obtained for pectin methylesterase and polygalacturonate hydrolase reported above. Hence, both extracellular and cell-bound enzymes appear as identical activities. Preliminary enzyme purification studies failed to separate the two activities by gel filtration on a Sephadex G200 column. Both pectin methylesterase and polygalacturonate hydrolase were recovered in one peak which corresponded to a molecular weight of 320,000.

Bibliography

1. Zeikus, J. G., *Enzyme Microb. Technol.* 1, 243 (1979).
2. Langeworthy, T. A., et al., *Strategies of Life in Extreme Environments* (Shilo, M., ed.) Dahlem Konferenzen, Berlin, 1979.
3. Brock, T. D. *Thermophilic Microorganisms and Life at High Temperatures,* Springer-Verlag, New York, 1978.
4. *Microbial Life in Extreme Environments,* (Kushner, D. J., ed.) Academic Press, London, 1978.

5. *Extreme Environments-Mechanisms of Microbial Adaptation* (Heinrich, M. R., ed.) Academic Press, New York, 1978.
6. *Biochemistry of Thermophily (Freidman, M., ed.)* Academic Press, New York, 1979.
7. *Symposium on Enzymes and Proteins from Thermophilic Microoganisms* (Zuber, H., ed.) Birkhauser-Verlag, Basel, 1976.
8. Ljungdahl, L. G. *Adv. Microb. Physiol.*, 19, 149 (1979).
9. Amelunxen, R. E., *CRTC Crit. Rev. Microbiol.*, 6, 343, 1978.
10. Tansey, M. R., et al., *Microbiol Life in Extreme Environments* (Kushner, D. J., ed.) Academic Press, London, 1978, p. 139.
11. Castenholz, R. W. in *Strategies of Life in Extreme Environments* (Shilo, M., ed.) Dahlem Konferenzen, Berlin, 1979.
12. Ben-Bassat A., et al., *Archives of Microbiology* 128, 365 (1981).
13. Wiegel, J. et al., *Archives Microbiology* 128, 343 (1981).
14. Zeikus, J. G., et al., *Archives of Microbiology* 122, 41 (1979).
15. Zeikus, J. G., et al., *Journal of Bacteriology* 143, 432 (1980).
16. Zeikus, J. G., *Annual Reviews of Microbiology* 34, 423 (1980).
17. Doemel, W. N., et al., *Applied and Environmental Microbiology* 34, 433 (1977).
18. Viljoen, J. A., et al., *Journal of Agricultural Science* 16, 1 (1926).
19. Ng, T. K., et al., *Archives of Microbiology* 114, 1 (1977).
20. Klaushofer, H., et al., *Zeitschrift fur Zuckerindustrie* 15, 445 (1965).
21. Mateuzzi, D., et al., *International Journal of Systematic Bacteriology* 28, 528 (1978).
22. Hsu, E. T., et al., *Journal of Bacteriology* 102, 364 (1970).
23. Fontaine, F. E., et al., *J. of Bacteriology* 43, 701 (1942).
24. Rombouts, F. M., et al., *Microbiol Enzymes and Bioconversions (Ross, A. H., Ed.) pp.* 228-282, Academic Press, Inc., New York (1980).
25. Rexova-Benkova, L., et al., *Adv. Carbohydrate Chem. Biochem.* 33, 323 (1976).
26. Schink, B., et al., *Appl. Environ. Micro.* 42, 526 (1981).
27. Schink, B., et al., *J. Gen. Microbiology,* 128, 2271 (1982).
28. Lund B. M., et al., *J. Gen. Microbiology* 104, 59 (1978).
29. MacMillan, J. D., et al., *Biochemistry* 3, 572 (1964).
30. Ng, T. K., et al., *Arch. Microbiol.* 114, 1 (1977).
31. Shink, B., et al., *Journal of General Microbiology.*
32. Postgate, J. R., *Applied Microbiology* 11, 265 (1963).
33. Kellenberger, E., et al., *J. of Biophysical and Biochemical Cytology* 4, 671 (1958).
34. Marmur, *J. of Molecular Biology* 3, 208 (1961).
35. DeLey, *J. of Bacteriology* 101, 738 (1970).
36. Lowry, *J. Biol. Chem.* 193, 265 (1951).
37. Nelson, D. R., et al., *Analytical Biochemistry* 1, 127 (1974).
38. Bergmeyer, H. U. *Methods of Enzymatic Analysis;* Weinheim, W. Germany: Verlag Chemie.
39. Miller, G. L. et al., *Analytical Biochemistry* 1, 127 (1960).
40. Szarkowska, *Biochemische Zeitschrift* 338, 674 (1963).
41. Pachmayr, Vorkommen and Bestimmung von Schwefelverbindungen in Mineral Wasser. Thesis, Univ. Munchen (1960).
42. Fliermanns, C. B., et al., *Soil Science* 115, 120 (1973).
43. Ffennig, N., *Annual Review of Microbiology* 21, 285 (1967).
44. Schedel, M., et al., *Archives of Microbiology* 124, 205 (1980).
45. Somoggi, L. P., et al., *Anal. Biochem.* 7, 4981 (1964).
46. Miller, G. L., et al., *J. Bacteriology* 102, 72 (1970).
47. Kurowski, W. M., et al., *Eur. J. Appl. Microbiol.* 2, 103 (1976).
48. Lowry, O. H., et al., *J. Biol. Chem.,* 193, 265 (1951).

I claim:

1. An enzyme product of *Clostridium thermosulfurogenes* displaying pectinolytic activity which loses no activity upon heating at a temperature of 60° C. for a period of 30 minutes.

2. The enzyme product of claim 1 wherein the pectinolytic activity is present in a cell extract comprising polygalacturonate hydrolase and pectin methyl-esterase.

3. The product of claim 2 wherein the pH optima of the polygalacturonate hydrolase and pectin methyl-esterase are, respectively, pH 5.5 and 6.5.

* * * * *